United States Patent
Han et al.

(10) Patent No.: US 11,981,939 B2
(45) Date of Patent: May 14, 2024

(54) ENZYME COMPLEX FOR DECOMPOSING POLYETHYLENE TEREPHTHALATE AND MANUFACTURING METHOD THEREOF

(71) Applicant: Korea University Research and Business Foundation, Seoul (KR)

(72) Inventors: Sung Ok Han, Seoul (KR); Dong Hyeok Hwang, Hongseong-gun (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 17/933,675

(22) Filed: Sep. 20, 2022

(65) Prior Publication Data
US 2023/0111846 A1    Apr. 13, 2023

(30) Foreign Application Priority Data
Jul. 22, 2021 (KR) ......................... 10-2021-0096317

(51) Int. Cl.
| | |
|---|---|
| *C12N 9/18* | (2006.01) |
| *C07K 14/195* | (2006.01) |
| *C08J 11/10* | (2006.01) |
| *C12N 15/62* | (2006.01) |

(52) U.S. Cl.
CPC .............. *C12N 9/18* (2013.01); *C07K 14/195* (2013.01); *C08J 11/105* (2013.01); *C12N 15/62* (2013.01); *C12Y 301/01* (2013.01); *C12Y 301/01003* (2013.01); *C07K 2319/00* (2013.01); *C08J 2367/02* (2013.01)

(58) Field of Classification Search
None
See application file for complete search history.

(56) References Cited

FOREIGN PATENT DOCUMENTS

KR    10-2020-0067665    6/2020

OTHER PUBLICATIONS

Chica et al. Curr Opin Biotechnol. Aug. 2005;16(4):378-84. (Year: 2005).*
Singh et al. Curr Protein Pept Sci. 2018;19(1):5-15 (Year: 2018).*
Accession A0A0K8P6T7. May 11, 2016 (Year: 2016).*
Accession B6DAC2. Nov. 25, 2008 (Year: 2008).*
Accession D9SS73. Oct. 5, 2010 (Year: 2010).*
Accession P38058. Oct. 1, 1994 (Year: 1994).*
Oliveira, Carla, et al. "Recombinant CBM-fusion technology—Applications overview." Biotechnology Advances 33.3-4 (2015): 358-369.
Weber, Joanna, et al. "Interaction of carbohydrate-binding modules with poly (ethylene terephthalate)." Applied Microbiology and Biotechnology 103 (2019): 4801-4812.
Duarte, Marlene, et al. "A dual cohesin-dockerin complex binding mode in *Bacteroides cellulosolvens* contributes to the size and complexity of its cellulosome." Journal of Biological Chemistry 296, Mar. 18, 2021, (13 pages).
Korean Office Action issued on Jun. 27, 2023, in counterpart Korean Patent Application No. 10-2021-0096317 (2 pages in English, 3 pages in Korean).
Korean Office Action issued on Aug. 22, 2023, in counterpart Korean Patent Application No. 10-2021-0096317 (1 pages in English, 2 pages in Korean).

* cited by examiner

*Primary Examiner* — Christian L Fronda
(74) *Attorney, Agent, or Firm* — NSIP Law

(57) ABSTRACT

Provided are an enzyme complex for decomposing polyethylene terephthalate (PET), a method for decomposing waste plastic using the enzyme complex, and a manufacturing method of the enzyme complex. According to the present disclosure, since the enzyme complex is a complex form of *Ideonella sakaiensis*-derived PETase and *Candida Antarctica*-derived lipase (CALB) by dockerin-cohesin binding and is simultaneously applicable to a substrate to be decomposed, it is possible to exhibit a synergistic effect on the decomposition of polyethylene terephthalate. In addition, it is possible to provide a stable enzyme complex of decomposing polyethylene terephthalate by providing a mini-scaffolding protein obtained by miniaturizing cellulosome as a scaffolding protein. In particular, the mini-scaffolding protein includes an A-type CBM3 module as a carbohydrate binding module to increase the accessibility to polyethylene terephthalate, a substrate to be decomposed, and to have quickly and efficiently polyethylene terephthalate decomposition activity.

4 Claims, 6 Drawing Sheets

Specification includes a Sequence Listing.

ENZYME COMPLEX FOR DECOMPOSING POLYETHYLENE TEREPHTHALATE AND MANUFACTURING METHOD THEREOF

CROSS-REFERENCE TO RELATED APPLICATION

This present application claims the benefit of priority to Korean Patent Application No. 10-2021-0096317, entitled "Enzyme complex for decomposing polyethylene terephthalate and manufacturing method thereof," filed on Jul. 22, 2021, in the Korean Intellectual Property Office, the entire disclosure of which is incorporated herein by reference.

FIELD

The present disclosure relates to an enzyme complex for decomposing polyethylene terephthalate (PET), a method for decomposing waste plastic using the enzyme complex, and a manufacturing method of the enzyme complex.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system and which is hereby incorporated by reference in its entirety for all purposes. The xml file submitted herewith contains a 48 KB file, MISC20220928_0181810003_SequenceListing_Updated, which was created on Oct. 27, 2022.

BACKGROUND

Plastics are useful polymers manufactured based on chemical components and have disadvantage of being hardly decomposed naturally.

One type of plastic, polyethylene terephthalate (PET), is a polymer consisting of ethylene glycol and terephthalate, and has ester bonds between the two chemical components and the polymer is formed based on forms such as mono hydroxy ethyl terephthalate and bis hydroxy ethyl terephthalate.

A physical method of reacting under high temperature and high pressure conditions is the most used plastic treatment method, but has another problem by emitting secondary environmental pollutants. Accordingly, interest in environmental biological treatment methods rather than the physical method is increasing.

On the other hand, the biological treatment method is a method of decomposing plastics using insects, bacteria, etc., and as related enzymes have been identified, studies on biological decomposition have been actively conducted.

The decomposition process of polyethylene terephthalate (PET) is performed by converting the PET to bis(2-hydroxyethyl) terephthalate (BHET) and mono(2-hydroxyethyl) terephthalate (MHET) to be converted to terephthalate (TPA) and ethylene glycol (EG) as monomers. As the enzyme that decomposes the PET to convert to BHET and MHET, cutinase, PETase, lipase, and the like have been studied.

Meanwhile, as the most abundant biomass in nature, an enzyme for decomposing cellulose is produced by fibrous mold or various bacteria, but among the bacteria, it is known that an anaerobic strain, clostridias, produces an enzyme complex using domains called cohesin and dockerin. The enzyme complex has several cohesion domains in a scaffolding protein to be formed by binding to enzymes having the dockerin domain, and has a carbohydrate binding module (hereinafter, simply abbreviated as 'CBM') in the scaffolding protein to improve the efficiency of enzymes forming the complex. An enzyme with dockerin capable of forming the enzyme complex is called a chimeric enzyme, but various types of enzymes may be arbitrarily attached by using an enzyme recombined with a dockerin domain capable of binding to a specific cohesin, so that the complex may be formed by arbitrarily selecting an enzyme according to the purpose.

Under this background, the present inventors have attempted to develop an enzyme complex technology capable of effectively and biologically decomposing polyethylene terephthalate. As a result, a recombinant protein was prepared by fusing a dockerin module of *Clostridium cellulovorans*-derived endo-β-1,4-Glucanase-B to *Ideonella sakaiensis*-derived PETase and *Candida antarctica*-derived lipase (*C. antarctica* lipase 1B, hereinafter abbreviated as 'CALB'), respectively. In addition, an enzyme complex for decomposing polyethylene terephthalate linked by dockerin-cohesin binding was prepared using a mini-scaffolding protein including a cohesin module capable of binding to the dockerin module of these proteins. Then, the present inventors confirmed that such an enzyme complex effectively decomposed polyethylene terephthalate and then completed the present disclosure.

SUMMARY

An aspect of the present disclosure is to provide an enzyme complex capable of effectively decomposing polyethylene terephthalate.

Another aspect of the present disclosure is to provide a method for decomposing waste plastic using the enzyme complex for decomposing polyethylene terephthalate.

Yet another aspect of the present disclosure is to provide a method for manufacturing the enzyme complex for decomposing polyethylene terephthalate.

According to an exemplary embodiment of the present disclosure, there is provided an enzyme complex for decomposing polyethylene terephthalate, in which a fusion protein 1 to which PETase and a dockerin module bind; and a fusion protein 2 to which lipase and a dockerin module bind; are linked to a mini-scaffolding protein including a cohesin module and a carbohydrate binding module by dockerin-cohesin binding.

In the exemplary embodiment, the fusion protein 1 may be represented by an amino acid sequence of SEQ ID NO: 1.

In the exemplary embodiment, the fusion protein 2 may be represented by an amino acid sequence of SEQ ID NO: 3.

In the exemplary embodiment, the carbohydrate binding module may be a carbohydrate-binding module family 3 (CBM3 module).

In the exemplary embodiment, the CBM3 module may be represented by an amino acid sequence of SEQ ID NO: 7.

In the exemplary embodiment, the mini-scaffolding protein including the cohesin module and the carbohydrate binding module may be represented by an amino acid sequence of SEQ ID NO: 5.

Further, the present disclosure provides a method for decomposing waste plastic including treating waste plastic with the enzyme complex for decomposing polyethylene terephthalate.

Further, the present disclosure provides a manufacturing method of an enzyme complex for decomposing polyethylene terephthalate including a) preparing a first transformant into which a vector including a gene encoding a fusion protein 1 to which PETase and a dockerin module bind is introduced, a second transformant into which a vector including a gene encoding a fusion protein 2 to which lipase and a dockerin module bind is introduced, and a third transformant into which a vector including a gene encoding a mini-scaffolding protein including a cohesin module and a carbohydrate binding module is introduced; b) culturing the first to third transformants in a medium; and c) separating a culture supernatant.

In the exemplary embodiment, the fusion protein 1 may be represented by an amino acid sequence of SEQ ID NO: 1.

In the exemplary embodiment, the fusion protein 2 may be represented by an amino acid sequence of SEQ ID NO: 3.

In the exemplary embodiment, the carbohydrate binding module may be a carbohydrate-binding module family 3 (CBM3 module).

In the exemplary embodiment, the CBM3 module may be represented by an amino acid sequence of SEQ ID NO: 7.

In the exemplary embodiment, the mini-scaffolding protein including the cohesin module and the carbohydrate binding module may be represented by an amino acid sequence of SEQ ID NO: 5.

In the exemplary embodiment, the first to third transformants may be *Escherichia coli* BL21 (DE3).

According to the present disclosure, since the enzyme complex is a complex form of *Ideonella sakaiensis*-derived PETase and *Candida antarctica*-derived lipase (CALB) by dockerin-cohesin binding and is simultaneously applicable to a substrate to be decomposed, it is possible to exhibit a synergistic effect on the decomposition of polyethylene terephthalate. In addition, it is possible to provide a stable enzyme complex of decomposing polyethylene terephthalate by providing a mini-scaffolding protein obtained by miniaturizing cellulosomes as a scaffolding protein. In particular, the mini-scaffolding protein includes an A-type CBM3 module as a carbohydrate binding module to increase the accessibility to polyethylene terephthalate, a substrate to be decomposed, and to have quickly and efficiently polyethylene terephthalate decomposition activity.

In addition, the enzyme complex of the present disclosure can be used as a new technology in the polyethylene terephthalate recycling market, which is continuously growing, so that it is expected to be the invention of an enzyme agent which is economically cheaper than chemical treatment methods and is environmentally safe. In addition, it is expected to create additional profits by securing terephthalic acid and ethylene glycol, which may be used as precursors and chemical materials in various industries through the recycling of polyethylene terephthalate.

BRIEF DESCRIPTION OF THE DRAWINGS

The above and other aspects, features, and advantages of the present disclosure will become apparent from the detailed description of the following aspects in conjunction with the accompanying drawings, in which.

DETAILED DESCRIPTION

Figure 1A:
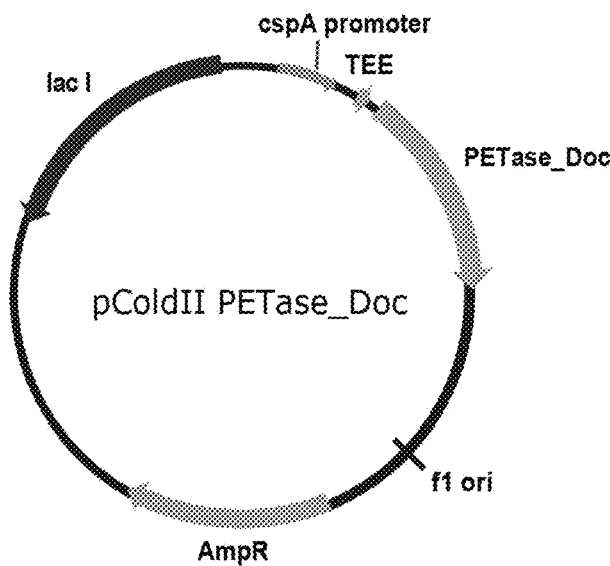
FIG. 1A is a schematic diagram of a recombinant vector pColdII PETase Doc in the present disclosure into which a gene bound with PETase derived from *Ideonella sakaiensis* and a dockerin module derived from *Clostridium cellulovorans* is inserted.

Advantages and features of the present disclosure and methods for achieving them will become apparent from the descriptions of aspects herein below with reference to the accompanying drawings. However, the present disclosure is not limited to the aspects disclosed herein but may be implemented in various different forms. The aspects are provided to make the description of the present disclosure thorough and to fully convey the scope of the present disclosure to those skilled in the art. It is to be noted that the scope of the present disclosure is defined only by the claims.

The present disclosure relates to an enzyme complex for decomposing polyethylene terephthalate in which a fusion protein 1 to which PETase and a dockerin module bind; and a fusion protein 2 to which lipase (CALB) and a dockerin module bind are linked to a mini-scaffolding protein including a cohesin module and a carbohydrate binding module by dockerin-cohesin binding.

In the present disclosure, the "PETase" is an esterase enzyme that catalyzes the hydrolysis of polyethylene terephthalate (PET) plastic to a monomer, mono-2-hydroxyethyl terephthalate (MHET).

In the present disclosure, the "dockerin" is a protein domain found in a cellulosome cell structure of anaerobic bacteria, and is often found in an endoglucanase enzyme. A binding partner of the dockerin is a cohesin domain located in a scaffoldin protein, and such an interaction between the dockerin domain of an enzymatic component of the cellulosome and the cohesin domain of the scaffoldin protein is required for a component of a cellulosome complex. In the present disclosure, the dockerin has the same meaning as the dockerin module or dockerin domain.

In the present disclosure, the "fusion protein 1" refers to a fusion protein in which the dockerin module binds to a PETase protein, and refers to a PETase recombinant protein.

In the present disclosure, the "fusion protein 2" refers to a fusion protein in which the dockerin module binds to a lipase (CALB) protein, and refers to a lipase (CALB) recombinant protein.

In the present disclosure, the "cohesin" is a domain that functions to bind to a mini-scaffolding protein by interacting with the dockerin. In the present disclosure, the cohesin has the same meaning as the cohesin module or cohesin domain.

In the present disclosure, the "carbohydrate binding module (CBM)" is a protein domain found in a carbohydrate active enzyme (e.g., glycoside hydrolase), and most of these domains have carbohydrate binding activity. Some of these domains are found in a cellulose scaffoldin protein. The CBM was previously known as a cellulose binding domain. The CBM is classified into numerous families according to amino acid sequence similarity, and it is known that there are 64 CBM families in a CAZy database based on June, 2011.

On the other hand, the cellulosome is formed by binding between a dockerin domain of one cellulosome-forming enzyme and one of several cohesin domains of a support protein. However, natural cellulosomes are very large in size to be difficult to be prepared and used. Accordingly, in the present disclosure, the natural cellulosome is miniaturized to provide a scaffolding protein of the enzyme complex for decomposing polyethylene terephthalate, which is called a mini-scaffolding protein.

In the present disclosure, the "mini-scaffolding protein (miniCbpA: mCbpA)" refers to a protein constituting the scaffolding of the enzyme complex for decomposing polyethylene terephthalate of the present disclosure.

The mini-scaffolding protein of the present disclosure includes a carbohydrate binding module (CBM) together with the cohesin module to perform a function of improving accessibility to the substrate to be decomposed of the enzyme complex, that is, polyethylene terephthalate.

The enzyme complex of the present disclosure is a complex in which three proteins are linked to each other, and specifically, consists of a fusion protein 1 to which PETase and a dockerin module bind; a fusion protein 2 to which lipase (CALB) and a dockerin module bind; and a mini-scaffolding protein including a cohesin module and a carbohydrate binding module. The dockerin domains of the fusion proteins 1 and 2 may be bound to the cohesin domain of the mini-scaffolding protein to form a complex.

The PETase may be PETase derived from *Ideonella sakaiensis*, which has SEQ ID NO: 8 or sequence homology of 70% or more, preferably 80% or more, more preferably 90% or more, much more preferably 95% or more thereto, and may consist of an amino acid sequence exhibiting a function substantially equivalent to the amino acid sequence represented by SEQ ID NO: 8.

The lipase may be lipase (CALB) derived from *Candida antarctica*, which has SEQ ID NO: 10 or sequence homology of 70% or more, preferably 80% or more, more preferably 90% or more, much more preferably 95% or more thereto, and may consist of an amino acid sequence exhibiting a function substantially equivalent to the amino acid sequence represented by SEQ ID NO: 10.

The dockerin module may be a dockerin module derived from *Clostridium cellulovorans*, which has SEQ ID NO: 12 or sequence homology of at 70% or more, preferably 80% or more, more preferably 90% or more, much more preferably 95% or more thereto, and may consist of an amino acid sequence exhibiting a function substantially equivalent to the amino acid sequence represented by SEQ ID NO: 12.

The carbohydrate binding module may be a carbohydrate binding module family 3 (CBM3 module) derived from *Clostridium cellulovorans*, which has SEQ ID NO: 7 or sequence homology of 70% or more, preferably 80% or more, more preferably 90% or more, much more preferably 95% or more thereto, and may consist of an amino acid sequence exhibiting a function substantially equivalent to the amino acid sequence represented by SEQ ID NO: 7.

In an exemplary embodiment of the present disclosure, the fusion protein 1 has SEQ ID NO: 1 or sequence homology of 70% or more, preferably 80% or more, more preferably 90% or more, much more preferably 95% or more thereto, and may consist of an amino acid sequence exhibiting a function substantially equivalent to the amino acid sequence represented by SEQ ID NO: 1.

In another exemplary embodiment of the present disclosure, the fusion protein 2 has SEQ ID NO: 3 or sequence homology of 70% or more, preferably 80% or more, more preferably 90% or more, much more preferably 95% or more thereto, and may consist of an amino acid sequence exhibiting a function substantially equivalent to the amino acid sequence represented by SEQ ID NO: 3.

In yet another exemplary embodiment of the present disclosure, the mini-scaffolding protein has SEQ ID NO: 5 or sequence homology of 70% or more, preferably 80% or more, more preferably 90% or more, much more preferably 95% or more thereto, and may consist of an amino acid sequence exhibiting a function substantially equivalent to the amino acid sequence represented by SEQ ID NO: 5.

In the present disclosure, the "functional equivalent" has sequence homology of at least 70% or more, preferably 80% or more, more preferably 90% or more, much more preferably 95% or more with the amino acid sequence represented by SEQ ID NO: as a result of the addition, substitution or deletion of the amino acid, and refers to a protein having substantially homogeneous physiological activity with the protein represented by the SEQ ID NO.

The enzyme complex of the present disclosure in the form of the fusion proteins 1 and 2 and the mini-scaffolding protein are mixed has the decomposition activity of polyethylene terephthalate (PET) and may be usefully used to decompose various types of waste including PET, such as packaging materials, films, plastic bottles, household goods, and toys.

In addition, the present disclosure provides a method for decomposing waste plastic, including treating waste plastic with the enzyme complex for decomposing polyethylene terephthalate.

In an exemplary embodiment of the present disclosure, the method for decomposing the waste plastic may be performed by fragmenting polyethylene terephthalate-based waste plastic to be decomposed into a predetermined size, treating the enzyme complex of the present disclosure, and then decomposing the waste plastic under a temperature condition of 20° C. to 37° C. for 1 hour to 10 days through an enzymatic reaction.

Further, the present disclosure provides a manufacturing method of an enzyme complex for decomposing polyethylene terephthalate including a) preparing a first transformant into which a vector including a gene encoding a fusion protein 1 to which PETase and a dockerin module bind is introduced, a second transformant into which a vector including a gene encoding a fusion protein 2 to which lipase (CALB) and a dockerin module bind is introduced, and a third transformant into which a vector including a gene encoding a mini-scaffolding protein including a cohesin module and a carbohydrate binding module is introduced; b) culturing the first to third transformants in a medium; and c) separating a culture supernatant.

Figure 1B:
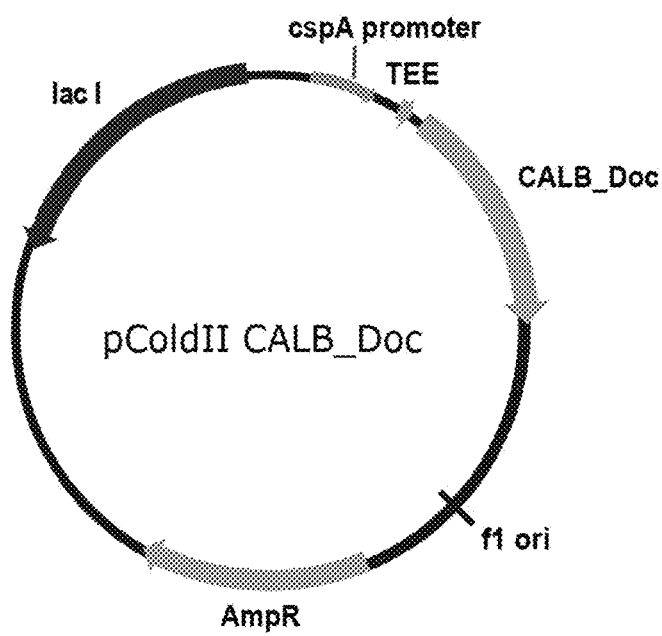
FIG. 1B is a schematic diagram of a recombinant vector pColdII CALB Doc in the present disclosure into which a gene bound with lipase (CALB) derived from *Candida antarctica* and a dockerin module derived from *Clostridium cellulovorans* is inserted.
Figure 1C:
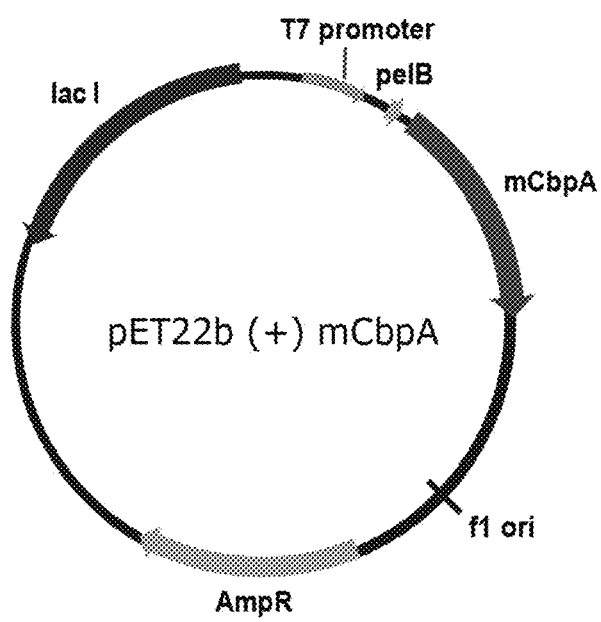
FIG. 1C is a schematic diagram of a recombinant vector pET22b-mCbpA in the present disclosure into which a gene including a CBM3 module derived from *Clostridium thermocellum* and two cohesin modules derived from *Clostridium cellulovorans* is inserted.

In the manufacturing method of the enzyme complex of the present disclosure, step a) is a step of preparing the first to third transformants, and particularly, a step of preparing a recombinant expression vector in which each gene coding (encoding) the fusion proteins 1 and 2 and the mini-scaffolding protein was cloned into a plasmid (see FIGS. 1A to 1C), and preparing each transformant by injecting each prepared recombinant expression vector into *E. coli*.

In the polynucleotide coding (encoding) each of the fusion proteins 1 and 2 and the mini-scaffolding protein of the present disclosure, due to the degeneracy of codons or in consideration of codons preferred in an organism in which the protein is to be expressed, it will be well understood by those skilled in the art that various modifications may be made to a coding region within a range without changing the amino acid sequence of the protein to be expressed from the coding region, various modifications or changes may be made within a range without affecting the expression of the gene even in parts other than the coding region, and such modified genes are also included within the scope of the present disclosure. That is, as long as the polynucleotide of the present disclosure encodes a protein having equivalent activity thereto, one or more nucleic acid bases may be mutated by substitution, deletion, insertion, or a combination thereof, which are also included in the scope of the present disclosure.

In an exemplary embodiment of the present disclosure, the fusion protein 1 may be a nucleotide sequence represented by SEQ ID NO: 2; the fusion protein 2 may be a nucleotide sequence represented by SEQ ID NO: 4; and the mini-scaffolding protein may be a nucleotide sequence represented by SEQ ID NO: 6.

In the present disclosure, as the "vector" into which the gene may be cloned, a pColdII plasmid is used for the fusion proteins 1 and 2, and a pET22b plasmid is used for the mini-scaffolding protein, but in the case of a DNA product containing a DNA sequence operably linked to a suitable regulatory sequence capable of expressing DNA in a suitable host, the vector is not limited thereto. Thus, the vector may be a plasmid, a phage particle, or simply, a potential genomic insert. When transformed into an appropriate host, the vector can replicate and function independently of a host genome, or can be integrated into the genome itself in some cases. Since the plasmid is the most commonly used form of the current vector and a form used in a specific embodiment of the present disclosure, the "plasmid" and the "vector" are sometimes used interchangeably in the specification of the present disclosure. However, the present disclosure includes other forms of vectors that have equivalent functions which have been known or are to be known in the art.

As used herein, the "recombinant expression vector" is a recombinant carrier into which a heterologous DNA fragment is generally inserted, and generally refers to a double-stranded DNA fragment. Here, the heterologous DNA refers to heteromorphous DNA, which is DNA not found naturally in a host cell. When the expression vector is once present in the host cell, the expression vector may replicate independently of host chromosomal DNA and several copies of the vector and its inserted (heterologous) DNA may be produced.

The vector may include a promoter operatively linked to the gene to be cloned, and in the present disclosure, the "promoter" promotes the expression of a gene to be transfected, and the promoter may further include not only a basic element necessary for transcription, but also an enhancer that may be used to promote and regulate the expression.

In addition, in the present disclosure, the "transformation" or "transfection" means that DNA is introduced into a host so that the DNA is an extrachromosomal factor or replicable by chromosomal integration completion.

In an exemplary embodiment of the present disclosure, the host cell into which the recombinant expression vector is introduced may be *Escherichia coli* BL21 (DE3).

In the manufacturing method of the enzyme complex of the present disclosure, step b) is a step of culturing the first to third transformants prepared through step a) in the medium, and particularly, may induce the protein expression while inoculating the recombinant strains (first to third transformants) into the culture medium and then culturing the recombinant strains at 15 to 37° C. for 16 to 24 hours.

In the manufacturing method of the enzyme complex of the present disclosure, step c) is a step of separating the culture supernatant, and particularly, may centrifuge the culture solution cultured in step b) to collect cells and then lyze and centrifuge the cells to separate a supernatant. The enzyme complex of the present disclosure may be purified from the separated supernatant by using a His-tag linked to a C-terminal of the protein.

Hereinafter, the present disclosure will be described in more detail with reference to Examples. However, these Examples are only illustrative the present disclosure, and the scope of the present disclosure is not limited to these Examples.

Example 1

Securing of PETase, Lipase (CALB) and Dockerin Genes

A primer set having nucleotide sequences of SEQ ID NOs: 14 and 15 was prepared with reference to a nucleotide sequence (SEQ ID NO: 9) of a PETase gene from gDNA of *Ideonella sakaiensis*, and the PETase gene was amplified using the primer set.

A primer set having nucleotide sequences of SEQ ID NOs: 16 and 17 was prepared with reference to a nucleotide sequence (SEQ ID NO: 11) of a *C. antarctica* lipase 1B (hereinafter, briefly abbreviated as 'CALB') gene from gDNA of *Candida antarctica*, and the CALB gene was amplified using the primer set.

In addition, a dockerin gene was amplified using a primer set having nucleotide sequences of SEQ ID NOs: 18 (or 19) and 20 prepared with reference to a nucleotide sequence (SEQ ID NO: 13) of an endo-β-1,4-glucanase-B gene from a genome of *Clostridium cellulovorans*.

Example 2

Linkage of Gene of Dockerin Module and PETase and Lipase (CALB) Genes

The gene of the dockerin module of fibrinogenase obtained in <Example 1> and the amplified product of the PETase and lipase (CALB) genes were electrophoresed on a 0.8% agarose gel, and DNA fragments on the agarose gel were recovered using a gel extraction kit (GeneAll).

Overlap PCR was performed to prepare DNA fragments to which each gene of the PETase and the lipase (CALB) and the dockerin gene were linked. Specifically, a PCR reaction was performed by using a primer set for recombinant PETase of SEQ ID NOs: 21 to 24 and a primer set for recombinant lipase (CALB) of SEQ ID NOs: 25 to 28 from the two recovered DNA (PETase (or lipase (CALB))+dockerin) fragments. The primer set was prepared so that 5' of a forward primer included the PETase (or lipase (CALB)) gene and a restriction enzyme KpnI recognition sequence of a pColdII vector and 3' overlapped by 15 bp based on a connector part of the dockerin module; and designed so that 5' of a backward primer overlapped by 15 bp with a sequence after the PETase (or lipase (CALB)) and 3' included a restriction enzyme PstI recognition sequence and a sequence before the dockerin included in the pColdII vector. An overlap PCR reaction was performed at 94° C. for 2 minutes, and then a 10 cycle reaction was performed at 94° C. for 30 seconds, 56° C. for 1 minute and 30 seconds, and 72° C. for 5 minutes, respectively, and finally at 72° C. for 5 minutes.

As a result of performing the PCR reaction, the genes of 1050 bp of the 'recombinant PETase linked to the gene of the dockerin module' and 1218 bp of the 'recombinant lipase (CALB) linked to the gene of the dockerin module' were amplified (see SEQ ID NOs: 2 and 4). In the present disclosure, the recombinant genes were named 'PETase Doc' and 'CALB Doc', respectively.

Example 3

Preparation of Recombinant PETase and Recombinant Lipase (CALB) Expression Vectors and Transformants to which Each Gene of PETase and Lipase (CALB) and Dockerin Gene are Linked The 'PETase Doc' and 'CALB Doc' gene amplification products obtained in <Example 2> were confirmed on a 0.8% agarose gel by electrophoresis, and recovered using a PCR purification kit (Geneall).

Then, the recovered DNA fragments and pColdII vector were cleaved with KpnI and PstI restriction enzymes, and ligated at 25° C. for 2 hours using a T4 ligase kit (Enzynomics) to prepare a recombinant plasmid, and simultaneously transformed into *Escherichia coli* DH5α. Thereafter, it was confirmed whether the recombinant vector was introduced or not through colony PCR. The identified colonies were grown in an LB medium containing ampicillin and chloroamphenicol, and recombinant plasmid DNA was isolated. A nucleotide sequence of the isolated recombinant plasmid was identified, and the recombinant plasmid vectors were named 'pColdII PETase Doc' and 'pColdII CALB Doc', respectively (see FIGS. 1A and 1B).

Thereafter, the recombinant plasmid vectors were injected into *E. coli* BL21 to prepare transformants, and the strains were named 'BL21(DE3)/PETase Doc' and 'BL21(DE3)/CALB Doc', respectively.

Example 4

Preparation of Mini-Scaffolding Protein Expression Vector and Transformant Including CBM3 Module and Cohesin Gene <4-1> Securing of Mini-Scaffolding Protein Gene Including Cohesin Gene In order to clone a mini-cellulose binding protein A (hereinafter, briefly abbreviated as 'mCbpA') gene having a CBM3 module and two cohesin modules of a cellulose-binding protein A which was a primary scaffolding subunit of *cellulovorans* derived from *Clostridium*, with reference to a nucleotide sequence, a restriction enzyme BamHI recognition sequence (ggatcc) was inserted into 5' of a forward primer (SEQ ID NO: 29), and a restriction enzyme XhoI recognition sequence (ctcgag) was inserted into a reverse primer (SEQ ID NO: 30), respectively, to synthesize primers.

As a result, a PCR band containing the mini-scaffolding protein gene mCbpA (SEQ ID NO: 6), which was a part of the cellulose-binding protein-A gene of 1647 bp *Clostridium*-derived *cellulovorans*, was confirmed (results not illustrated).

<4-2> Preparation of Mini-Scaffolding Protein Expression Vector and Transformant Including Cohesin Gene The mCbpA amplified product obtained in Example <4-1> was confirmed on a 0.8% agarose gel by electrophoresis, and recovered using a PCR purification kit (Geneall).

Then, the recovered mCbpA gene was inserted into a pET22b(+) vector and transformed into *E. coli* DH5α and then a sequence was identified.

The plasmid vector pET22b-mCbpA, of which the sequence has been identified, was injected into *Escherichia coli*, Rosetta BL21 for protein expression to prepare a transformant, and this strain was named 'R. BL21/mCbpA'.

Example 5

Expression of Recombinant PETase and Recombinant Lipase (CALB) Proteins in *E. coli* Transformants In order to confirm the expression of the enzyme protein of the transformant obtained in <Example 3> and the mini-scaffolding protein obtained in <Example 4>, purification using His-Tag or Flag-tag and SDS-PAGE were performed.

Figure 2:
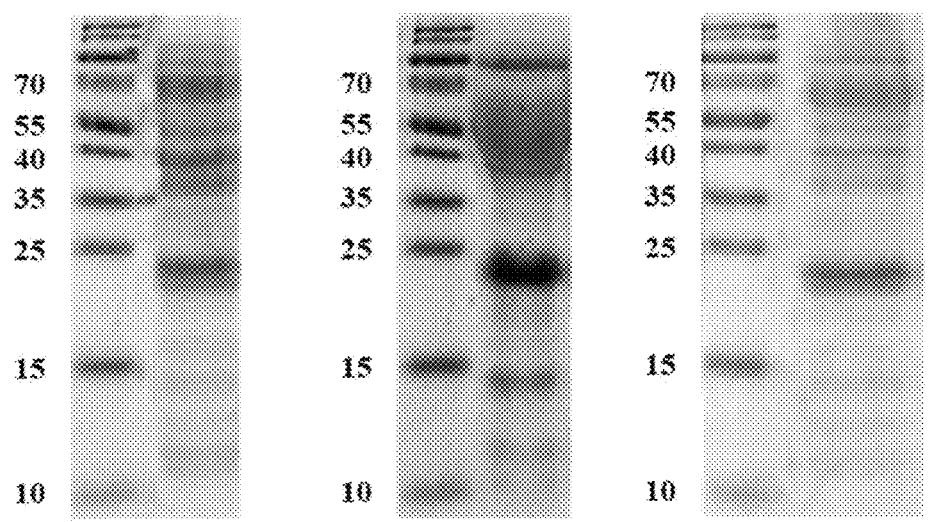
FIG. 2 is a result of confirming, through SDS-PAGE, respective proteins expressed in *E. coli* into which the recombinant vectors pColdII PETase Doc, pColdII CALB Doc, and pET22b-mCbpA provided in the present disclosure are inserted.

Recombinant strains BL21(DE3)/PETase Doc, BL21 (DE3)/CALB Doc, and R. BL21(DE3)/mCbpA were inoculated in an LB medium containing ampicillin after creating conditions for inducing protein expression of the recombinant strains, and cultured at 37° C. for 16 hours. Thereafter, after a 200 ml medium was made in a 500 ml Erlenmeyer shake flask and sterilized, the ampicillin and the recombinant strains are inoculated and cultured, and added with IPTG after an optical density was adjusted to 0.8 to induce protein expression at 15° C. for 24 hours. Cells inducing the protein expression were obtained by centrifugation, and these cells were lyzed using ultrasound and centrifuged to obtain a supernatant, and then the supernatant was purified and concentrated using His-tag linked to a C-terminal of the protein. Thereafter, 10% SDS-PAGE electrophoresis was performed, and it was confirmed that the proteins appeared at the same position as expected protein sizes by staining with Coomassie Blue (see FIG. 2).

Example 6

Confirmation of Decomposition Patterns of PETase and Lipase (CALB)

In order to confirm the decomposition patterns of PETase and lipase (CALB), a decomposition activity assay was performed using polyethylene terephthalate and bis-hydroxyethyl terephthalate as substrates.

In the enzyme activity assay method, in a reaction solution of 50 mM glycine-NaOH buffer (pH 9.0), polyethylene terephthalate cut into a size of 5 mm×5 mm and bis-hydroxyethylretephthalate with a final concentration of 700 μM were used as substrates and reacted at 30° C. for 1 to 7 days, and then the amount of terephthalic acid was analyzed through HPLC analysis.

Figure 3A:
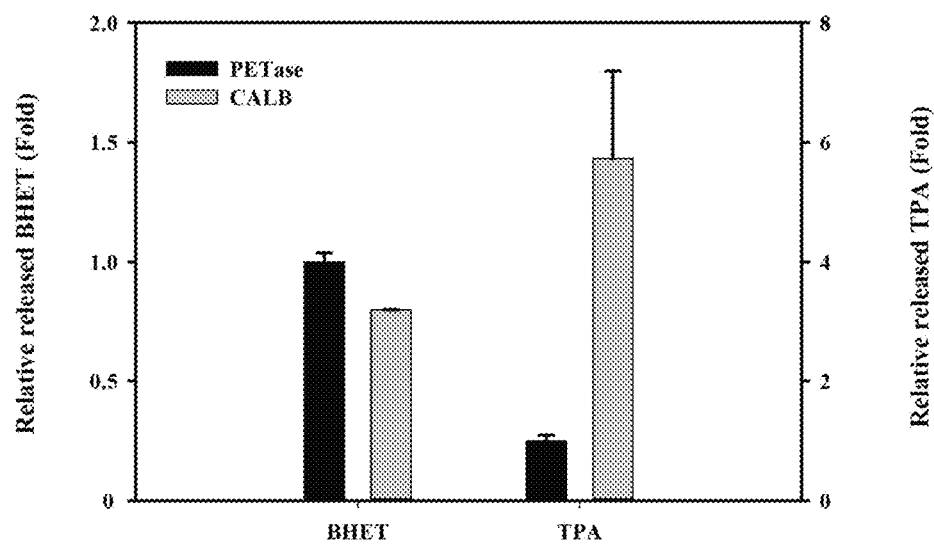
FIG. 3A is a result of confirming a reaction pattern according to treatment with two enzymes presented in the present disclosure, PETase and lipase (CALB), using a PET film as a substrate.
Figure 3B:
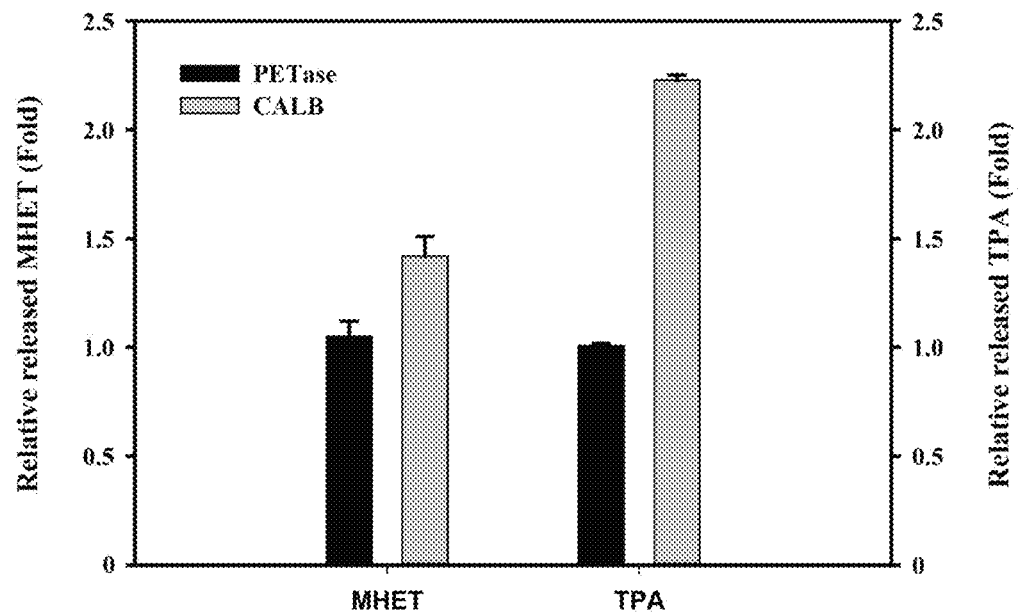
FIG. 3B is a result of confirming a reaction pattern according to treatment with two enzymes presented in the present disclosure, PETase and lipase (CALB), using BHET as a substrate.

As a result, as illustrated in FIG. 3, in a conversion reaction to bis-hydroxyethyl terephthalate (BHET) from a PET film, it was confirmed that PETase was better than lipase (CALB) (see FIG. 3A). On the other hand, in a reaction of converting bis-hydroxyethyl terephthalate (BHET) as a substrate to terephthalic acid (TPA), it was confirmed that the lipase (CALB) had a better reaction than PETase (see FIG. 3B).

Example 7

Confirmation of Adhesion to Polyethylene Terephthalate Using Carbon Binding Module The characteristic of the surface of polyethylene terephthalate was hydrophobic to hinder the access of enzymes. To solve this problem, three types of carbon-binding proteins (CBMs) were compared, and a protein with the best adhesion was used by grafting the complex. The carbon-binding proteins (CBMs) were classified into A type, B type, and C type according to a characteristic of a substrate to be bound. In the experiment, CBM3 as type A, CBM6 as type B, and CBM66 as type C were used for each type, respectively, and in these genes, CBM3 and CBM6 were obtained through *Clostridium thermocellum* and CBM66 were obtained through *Bacillus subtilis*, which were possessed in a laboratory. These genes were cloned using KpnI and BamHI, which were restriction enzyme sites inside each pcoldII vector, respectively, and the completed plasmid was transformed into a protein expression strain, Rosetta BL21 (DE3). The strains were inoculated in the LB medium containing an antibiotic, ampicillin and grown to OD 1 at 37° C., and induction was performed at 15° C. by adding IPTG. After 24 hours, the strains were collected by centrifugation and lyzed using an ultrasonicator to perform protein purification. The expression was confirmed through SDS-PAGE (results not illustrated). After confirming the expression, each type of protein was put in a buffer consisting of 50 mM Glycine-NaOH together with polyethylene terephthalate and reacted at 4° C. overnight. Thereafter, after twice washing, the proteins attached to the film were eluted through an elution solution, and the amounts of the remaining proteins were analyzed by Bradford analysis.

Figure 4A:
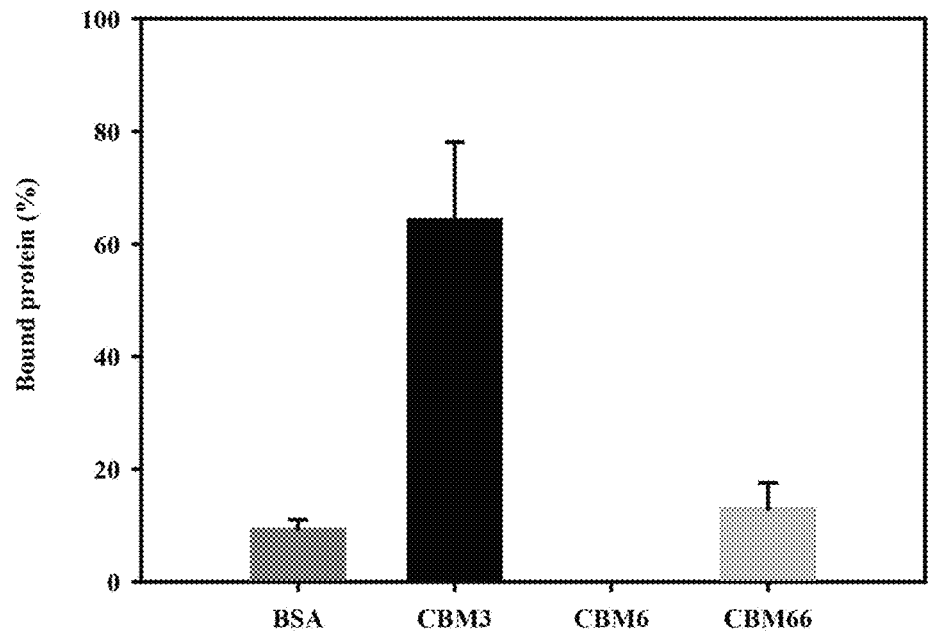
FIG. 4A is a result of comparing the adhesion with a PET film for each type of carbohydrate binding modules CBM3, CBM6, and CBM66, which are components of a complex.
Figure 4B:
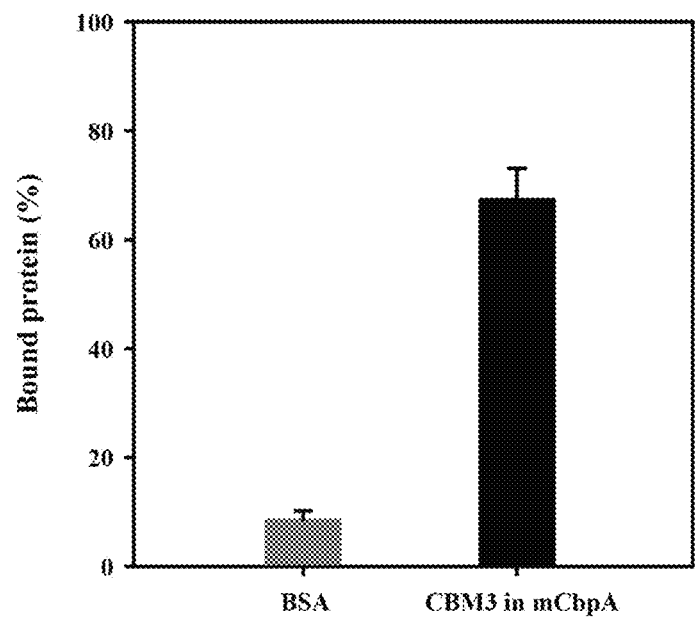
FIG. 4B is a result of confirming the improvement in adhesion of a mini-scaffolding protein mCbpA when a CBM3 module is actually applied.

As a result, as illustrated in FIG. 4, it was confirmed that CBM3 had the best adhesion to polyethylene terephthalate, and a CBM3-linked mini-scaffolding protein (mCbpA) also showed improved adhesion to the PET film.

Through the above results, it was expected that the enzyme complex of the present disclosure included the CBM3 module to help the reaction with the PET film.

Example 8

Formation of Complex Attached with Recombinant PETase and Recombinant Lipase (CALB) Proteins In order to confirm the formation of the enzyme protein complex of the transformant obtained in <Example 5>, the formation of the enzyme complex was observed using an interaction between the cellulose binding module and cellulose (results not illustrated).

In detail, in order to observe the formation of three types of enzyme complexes obtained in <Example 5>, for protein purification using the interaction between the cellulose-binding module (CBM) containing minicellulosomes and cellulose, cellulose (Sigmacell Type 50, SIGMA) was added and reacted at room temperature for 1 hour. After the reaction, the mixture was rinsed three times with 1 M sodium chloride and a 20 mM Tris buffer (pH 8.0) and eluted with a 50 mM Tris buffer (pH 12.5).

Example 9

PET Film Decomposing Effect of Enzyme Complex of the Present Disclosure

In order to confirm the degree of improvement in decomposition on the PET film of the enzyme complex of the present disclosure compared to single enzymes PETase and CALB and a simple mixture thereof, two experiments were conducted.

A buffer used was 50 mM glycine-sodium hydroxide (pH 9.0), and each of the single enzymes PETase and CALB, the simple mixture thereof, the enzyme complex of the present disclosure, and PET film pieces (5 mm×5 mm) were put in the buffer and then an enzymatic reaction thereof was performed at 30° C. for 1 to 7 days. The final concentration of each enzyme was uniformly applied as 50 nmol, and in the case of the mixture, PETase and lipase (CALB) were mixed in a 1:1 ratio. Each experiment was performed to confirm the results of the decomposition on the PET film in the enzyme complex of the present disclosure compared to the single enzymes and the safety of the enzyme during a long-term reaction. Samples after the reaction were analyzed by HPLC, but a mobile phase buffer A consisted of FDW containing 0.1% formic acid, and a mobile phase buffer B was prepared with FDW containing 20% acetonitrile. As the analysis conditions, the mobile phase buffer B was gradually changed in the proportion from 60% to 90% for 8 minutes, and flowed up to 100% for 16 minutes. In addition, finally, the buffer flowed until 25 minutes. The analysis wavelength was 260 nm.

Figure 5A:
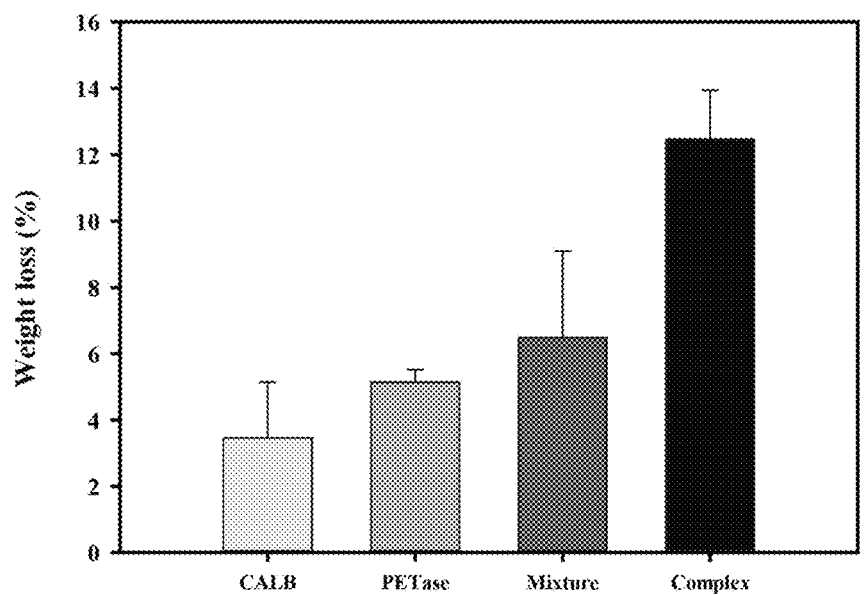
FIG. 5A illustrates a weight loss rate (%) of a PET film according to an enzymatic reaction for 7 days at 30° C. after single enzymes PETase and CALB, a simple mixture thereof, and the enzyme complex of the present disclosure are treated in the PET film, respectively.
Figure 5B:
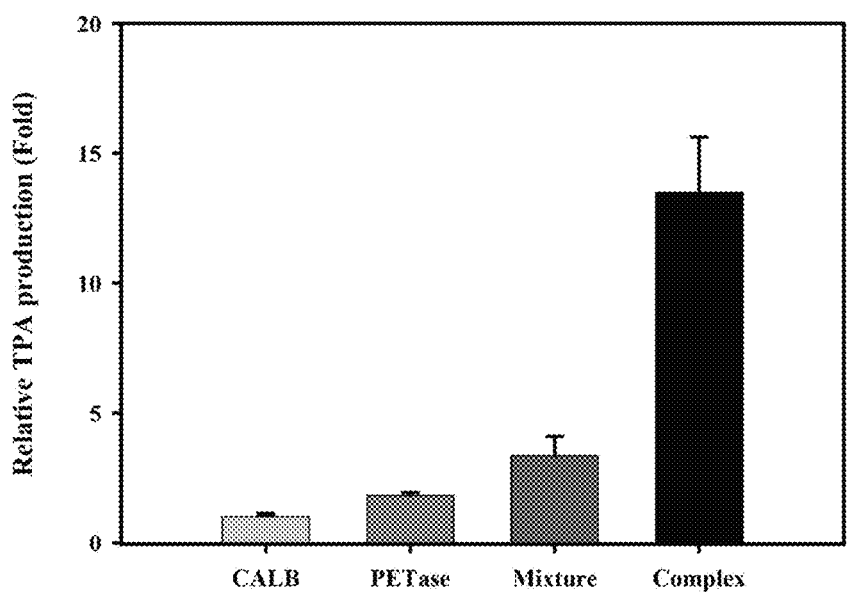
FIG. 5B illustrates an amount of conversion to terephthalic acid (TPA) according to an enzymatic reaction for 7 days at 30° C. after single enzymes PETase and CALB, a simple mixture thereof, and the enzyme complex of the present disclosure are treated in the PET film, respectively.

As a result, as illustrated in FIG. 5, it could be confirmed that when the enzyme complex of the present disclosure was treated, the decomposing effect of the PET film was remarkably better than a single enzyme (PETase, CALB)-treated group, and particularly, the decomposition activity of the PET film was remarkably excellent even compared to a simple mixture of single enzymes, PETase and CALB. That is, when comparing the weight loss of the PET film, the weight loss rate in the enzyme complex of the present disclosure was remarkably excellent compared to the single enzymes PETase and CALB and the simple mixture (see FIG. 5A), and similarly to the weight loss pattern of the PET film, the amount of conversion to terephthalic acid was highest in the enzyme complex (see FIG. 5B).

Figure 6:
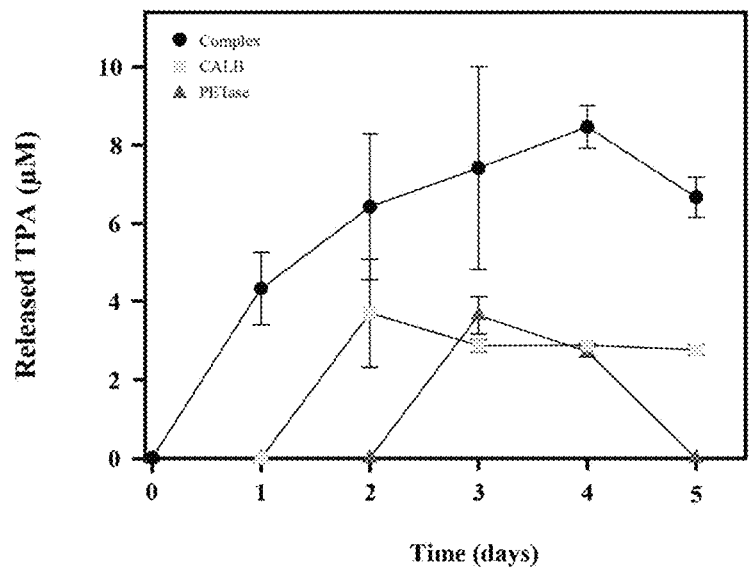
FIG. 6 illustrates an amount of conversion to terephthalic acid (TPA) according to an enzymatic reaction for 1 to 5 days at 30° C. after single enzymes PETase and CALB and the enzyme complex of the present disclosure are treated in a PET film, respectively.

In addition, as illustrated in FIG. 6, it was confirmed that in the case of the enzyme complex of the present disclosure, stability during a long-term reaction after treatment on the PET film was excellent compared to the single enzymes PETase and CALB.

TABLE 1

Amounts of PET film weight loss according to treatment with single enzymes (PETase, CALB), simple mixture thereof, and enzyme complex of the present disclosure

|  | CALB | PETase | Mixture | Complex |
|---|---|---|---|---|
| Average (%) | 3.46 | 5.14 | 6.49 | 12.47 |
| Standard deviation | 1.68 | 0.37 | 2.60 | 1.47 |

TABLE 2

Relative amounts of conversion to terephthalic acid (TPA) according to treatment with single enzymes (PETase, CALB), simple mixture thereof, and enzyme complex of the present disclosure

|  | CALB | PETase | Mixture | Complex |
|---|---|---|---|---|
| Average (%) | 6.18 | 11.22 | 20.72 | 83.38 |
| Standard deviation | 0.00 | 0.12 | 0.74 | 2.13 |

TABLE 3

Terephthalic acid concentration over time according to treatment with single enzymes (PETase, CALB) and enzyme complex of the present disclosure

|  | 1 day | 2 day | 3 day | 4 day |
|---|---|---|---|---|
| CALB | 0.00 ± 0.00 | 3.70 ± 1.39 | 2.86 ± 0.16 | 2.87 ± 0.03 |
| PETase | 0.00 ± 0.00 | 0.00 ± 0.00 | 3.64 ± 0.48 | 2.71 ± 0.13 |
| Complex | 4.33 ± 0.93 | 6.43 ± 1.86 | 7.42 ± 2.59 | 8.47 ± 0.59 |

Example 10

Actual Waste Plastic Decomposing Effect of Enzyme Complex of the Present Disclosure In order to confirm the actual waste plastic decomposition, a waste sprite bottle was obtained. In addition, the waste sprite bottle was washed and dried, and cut into a size of 5 mm×5 mm for an enzymatic reaction. In addition, the enzymatic reaction was performed in the same manner as in the enzymatic reaction conditions of <Example 9>. A final product was analyzed by HPLC, but a mobile phase buffer A consisted of FDW containing 0.1% formic acid, and a mobile phase buffer B was prepared with FDW containing 20% acetonitrile. As the analysis conditions, the mobile phase buffer B was gradually changed in the proportion from 60% to 90% for 8 minutes, and flowed up to 100% for 16 minutes. In addition, finally, the buffer flowed until 25 minutes. The analysis wavelength was 260 nm.

Figure 7:
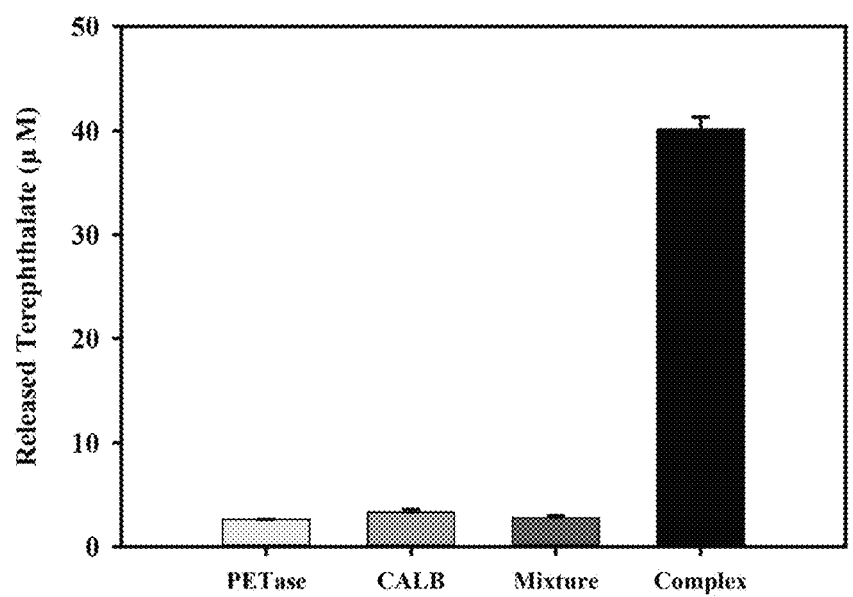
FIG. 7 illustrates an amount of conversion to terephthalic acid (TPA) according to an enzymatic reaction for 3 days at 30° C. after single enzymes PETase and CALB, a simple mixture thereof, and the enzyme complex of the present disclosure are treated in actual waste plastic (sprite bottle), respectively.

As a result, as illustrated in FIG. 7, it could be confirmed that in the case of treating the enzyme complex of the present disclosure by using actual waste plastic as a substrate, the amount of conversion to terephthalic acid was significantly excellent as compared to experimental groups treated with the single enzymes PETase and CALB and the simple mixture thereof.

TABLE 4

Amount (μM) of conversion to terephthalic acid using actual waste plastic as substrate

|  | CALB | PETase | Mixture | Complex |
|---|---|---|---|---|
| Average (%) | 3.30 | 2.63 | 2.77 | 40.15 |

The present disclosure described as above is not limited by the aspects described herein and accompanying drawings. It should be apparent to those skilled in the art that various substitutions, changes and modifications which are not exemplified herein but are still within the spirit and scope of the present disclosure may be made. Therefore, the scope of the present disclosure is defined not by the detailed description, but by the claims and their equivalents, and all variations within the scope of the claims and their equivalents are to be construed as being included in the present disclosure.

What is claimed is:

1. An enzyme complex for decomposing polyethylene terephthalate comprising:
   a fusion protein 1 comprising the amino acid sequence of SEQ ID NO: 1;
   a fusion protein 2 comprising the amino acid sequence of SEQ ID NO: 3; and
   a mini-scaffolding protein comprising the amino acid sequence of SEQ ID NO: 5 and comprising a cohesin module and a carbohydrate binding module comprising the amino acid sequence of SEQ ID NO: 7,
   wherein the fusion protein 1 comprises PETase and a dockerin module comprising the amino acid sequence of SEQ ID NO: 12,
   wherein the fusion protein 2 comprises lipase and the dockerin module comprising the amino acid sequence of SEQ ID NO: 12, and
   wherein the fusion protein 1 and the fusion protein 2 are linked to the mini-scaffolding protein by dockerin-cohesin binding.

2. A method for decomposing waste plastic comprising treating waste plastic with the enzyme complex for decomposing polyethylene terephthalate of claim 1.

3. A manufacturing method of the enzyme complex for decomposing polyethylene terephthalate of claim 1 comprising the steps of:
   a) preparing a first transformant into which a vector comprising a gene encoding the fusion protein 1 of claim 1, a second transformant into which a vector comprising a gene encoding the fusion protein 2 of claim 1, and a third transformant into which a vector comprising a gene encoding the mini-scaffolding protein of claim 1;
   b) culturing the first to third transformants in a medium to prepare the enzyme complex of claim 1; and
   c) separating the enzyme complex from a culture supernatant.

4. The manufacturing method of the enzyme complex for decomposing polyethylene terephthalate of claim 3, wherein the first to third transformants are *Escherichia coli* BL21 (DE3).

* * * * *

SEQUENCE LISTING

```
Sequence total quantity: 30
SEQ ID NO: 1             moltype = AA  length = 350
FEATURE                  Location/Qualifiers
REGION                   1..350
                         note = polypeptide sequence of fusion protein 1
source                   1..350
                         mol_type = protein
                         organism = synthetic construct
SEQUENCE: 1
MELGTXXXXQ TNPYARGPNP TAASLEASAG PFTVRSFTVS RPSGYGAGTV YYPTNAGGTV   60
GAIAIVPGYT ARQSSIKWWG PRLASHGFVV ITIDTNSTLD QPSSRSSQQM AALRQVASLN  120
GTSSSPIYGK VDTARMGVMG HSMGGGGSLI SAANNPSLKA AAPQAPWDSS TNFSSVTVPT  180
LIFACENDSI APVNSSALPI YDSMSRNAKQ FLEINGGSHF CANSGNSNQA LIGKKGAAWM  240
KRFMDNDTRY STFACENPNS TRVSDFRTAN CSLGSAGSAA GSGEFDVNKD GKVNAIDYAV  300
LKSILLGTNT NVDLSVSDMN KDGKVNALDL AVLKKMLLDY KDDDDKLQSR            350

SEQ ID NO: 2             moltype = DNA  length = 1050
FEATURE                  Location/Qualifiers
misc_feature             1..1050
                         note = polynucleotide sequence of fusion protein 1
source                   1..1050
                         mol_type = other DNA
                         organism = synthetic construct
```

```
SEQUENCE: 2
atggagctcg gtaccathga rggncgncag accaatccgt atgcgcgcgg ccccaaccct     60
accgccgcct cgttggaagc cagcgcggga ccctttaccg ttcgtagctt taccgttagc    120
cgtccgtccg gatatggtgc agggaccgtc tattacccaa ccaatgcagg cggcaccgtt    180
ggcgcgattg caatcgtccc cgggtacacc gcgcgtcaaa gcagcattaa gtggtggggt    240
ccgcgcttag ctagccatgg ctttgtggtt attaccatcg atacgaacag cactctagac    300
cagcccagca gccgtagctc gcaacagatg gccgcgcttc gtcaagttgc gagcttgaac    360
gggaccagca gtagcccgat ttacggaaag gtcgatactg cccgcatggg tgtgatgggc    420
cactcaatgg ggggcggcgg ttcacttatt agccgccgca acaacccgag tttaaaagca    480
gcggcaccgc aggcgccatg ggactcttca accaacttca cgagtgttac cgtgccgacg    540
ctgattttcg cgtcgcgaga atgatagcat tgcaccggtg acagcagcgc gctgccgatt    600
tatgatagca tgtcccgcaa cgcaaaacag tttctgaaaa ttaacggcgg tagccacttc    660
tgtgccaact ctgggaacag caaccaggca ctgatcggaa aaaaggggc tgcatggatg    720
aaacgattca tggataatga caccgttac tcaaccttcg cctgtgagaa tcccaacagc    780
acacgcgtgt cggattttcg caccgcgaac tgttccctcg gatccgctgg ctccgctgct    840
ggttctgggg aattcgatgt taacaaagat ggaaaggtaa atgctatcga ttatgcagtg    900
cttaaatcaa ttcttttagg tacaaatact aacgttgatt tatcagtatc agacatgaat    960
aaggatggta agtaaatgc tttggattta gctgttctta aaaaaatgct tttagattac   1020
aaggatgacg acgataagct gcagtctaga                                    1050

SEQ ID NO: 3              moltype = AA  length = 406
FEATURE                   Location/Qualifiers
REGION                    1..406
                          note = polypeptide sequence of fusion protein 2
source                    1..406
                          mol_type = protein
                          organism = synthetic construct
SEQUENCE: 3
MELGTXXXXA LPSGSDPAFS QPKSVLDAGL TCQGASPSSV SKPILLVPGT GTTGPQSFDS     60
NWIPLSTQLG YTPCWISPPP FMLNDTQVNT EYMVNAITAL YAGSGNNKLP VLTWSQGGLV    120
AQWGLTFFPS IRSKVDRLMA FAPDYKGTVL AGPLDALAVS APSVWQQTTG SALTTALRNA    180
GGLTQIVPTT NLYSATDEIV QPQVSNSPLD SSYLFNGKNV QAQAVCGPLF VIDHAGSLTS    240
QFSYVVGRSA LRSTTGQARS ADYGITDCNP LPANDLTPEQ KVAAAALLAP AAAAIVAGPK    300
QNCEPDLMPY ARPFAVGKRT CSGIVTPSLG SAGSAAGSGE FDVNKDGKVN AIDYAVLKSI    360
LLGTNTNVDL SVSDMNKDGK VNALDLAVLK KMLLDYKDDD DKLQSR                   406

SEQ ID NO: 4              moltype = DNA  length = 1218
FEATURE                   Location/Qualifiers
misc_feature              1..1218
                          note = polynucleotide sequence of fusion protein 2
source                    1..1218
                          mol_type = other DNA
                          organism = synthetic construct
SEQUENCE: 4
atggagctcg gtaccathga rggncgngca ttgccgtcag gttctgaccc ggcctttagc     60
cagccgaagt ctgttctgga tgctggcctg acatgtcagg gtgcaagccc gtcgtccgta    120
agcaaaccaa ttctgcttgt accaggcacg ggcactacgg gcccgcagag cttttgattct    180
aattggattc ccctgtctac ccagcttggg tacacccctt gttggattag cccgcctccc    240
ttcatgctga acgatacaca agtgaatact gagtacatgg tcaacgcaat taccgccctt    300
tatgcgggaa gtggtaacaa taaacttccc gtgctgacat ggagtcaggg gggcctggtg    360
gcacagtggg gattgacgtt ttttcccatcg atccgctca aagttgatcg tctgatgcca    420
tttgcgcctg attataaagg cacagtgctc gcggggccat tagatgccct ggctgtgtca    480
gcacctagtg tctggcaaca gacgaccggt tccgcgctga cgaccgccct ccggaacgca    540
ggtggactga cccaaattgt gccgacaacc aacttgtata cgccaccga cgaaattgtt    600
cagccgcagg tctccaattc gcctctcgat tcaagctatc tgtttaacgg caaaaatgta    660
caggcacagg ctgtttgcgg gccattattc gtcatcgacc atgccggtag cttaacctcc    720
cagttcagtt acgtggttgg tcgctctgcc ctgcgtagta ccacgggcca agcgcgctca    780
gcggactacg gtatcactga ttgcaatccg ttaccggcga atgacctgac tccggaacaa    840
aaggtagcgg ctgcggcttt gttagcgccg gccgccgcg cgattgtggc aggtcctaaa    900
caaaactgta accggatct gatgccctat gcccgtccgt ttgcggtcgg caaacgtact    960
tgctcaggta tcgttacgcc aagcttagga tccgctggct ccgctgctgg ttctgggaa   1020
ttcgatgtta caaagatgg aaaggtaaat gctatcgatt atgcagtgct taaatcaatt   1080
cttttaggta caaatactaa cgttgattta tcagtatcag acatgaataa ggatggtaaa   1140
gtaaatgctt tggatttagc tgttcttaaa aaaatgcttt tagattacaa ggatgacgac   1200
gataagctgc agtctaga                                                1218

SEQ ID NO: 5              moltype = AA  length = 571
FEATURE                   Location/Qualifiers
REGION                    1..571
                          note = Polypeptide sequence of mCbpA
source                    1..571
                          mol_type = protein
                          organism = synthetic construct
SEQUENCE: 5
MDIGINSDPN SAATSSMSVE FYNSNKSAQT NSITPIIKIT NTSDSDLNLN DVKVRYYYTS     60
DGTQGQTFWC DHAGALLGNS YVDNTSKVTA NFVKETASPT STYDTYVEFG FASGAATLKK    120
GQFITIQGRI TKSDWSNYTQ TNDYSFDASS STPVVNPKVT GYIGGAKVLG TAPGPDVPSS    180
IINPTSATFD KNVTKQADVK TTMTLNGNTF KTITDANGTA LNASTDYSVS GNDVTISKAY    240
LAKQSVGTTT LNFNFSAGNP QKLVITVVDT PVEAVTATIG KVQVNAGETV AVPVNLTKVP    300
```

```
AAGLATIELP LTFDSASLEV VSITAGDIVL NPSVNFSSTV SGSTIKLLFL DDTLGSQLIT    360
KDGVFATITF KAKAITGTTA KVTSVKLAGT PVVGDAQLQE KPCAVNPGTV TINPIDNRMQ    420
ISVGTATVKA GEIAAVPVTL TSVPSTGIAT AEAQVSFDAT LLEVASVTAG DIVLNPTVNF    480
SYTVNGNVIK LLFLDDTLGS QLISKDGVFV TINFKAKAVT STVTTPVTVS GTPVFADGTL    540
AEVQSKTAAG SVTINIGDPI AAALEHHHHH H                                  571

SEQ ID NO: 6            moltype = DNA   length = 1713
FEATURE                 Location/Qualifiers
misc_feature            1..1713
                        note = Polynucleotide sequence of mCbpA
source                  1..1713
                        mol_type = other DNA
                        organism = synthetic construct
SEQUENCE: 6
atggatatcg gaattaattc ggatccgaat tcggcagcga catcatcaat gtcagttgaa     60
ttttacaact ctaacaaatc agcacaaaca aactcaatta caccaataat caaaattact    120
aacacatctg acagtgattt aaatttaaat gacgtaaaag ttagatatta ttacacaagt    180
gatggtacac aaggacaaac tttctggtgt gaccatgctg gtgcattatt aggaaatagc    240
tatgttgata acactagcaa agtgacagca aacttcgtta aagaaacagc aagcccaaca    300
tcaacctatg atacatatgt tgaatttgga tttgcaagcg agcagctac tcttaaaaaa     360
ggacaattta taactattca aggaagaata acaaatcag actggtcaaa ctacactcaa     420
acaaatgact attcatttga tgcaagtagt tcaacagcaa ttgtaaatcc aaaagttaca    480
ggatatatag gtggagctaa agtacttggt acagcaccag tccagatgt accatcttca     540
ataattaatc ctacttctgc aacatttgat aaaaatgtaa ctaaacaagc agatgttaaa    600
actactatga ctttaaatgg taacacattt aaaacaatta cagatgcaaa cggtacagct    660
ctaaatgcaa gcactgatta tagtgtttct ggaaatgtta taacaataag caaagcttat    720
ttagcaaaac aatcagtagg aacaactaca ttaaacttta actttagtgc aggaaatcct    780
caaaaattag taattacagt agttgacaca ccagttgaag ctgtaacagc tacaattgga    840
aaagtacaag taaatgctgg agaaacggta gcagtaccag ttaacttaac aaaagttcca    900
gcagctggtt tagcaacaat tgaattacca ttaacttttg attctgcatt attagaagta    960
gtatcaataa ctgctggaga tatcgtatta aatccatcag taaacttctc ttctacagta   1020
agtggaagca caataaaatt attattctta gatgatacat taggaagcca attaatcact   1080
aaggatggag tttttgcaac aataacattt aaagcaaaag ctataactgg aacaactgca   1140
aaagtaactt cagttaaatt agctggaaca ccagtgctg gtgatgcgca attacaagaa    1200
aaaccttgtg cagttaaccc aggaacagta actatcaatc aatcgataa tagaatgcaa    1260
atttcagttg gaacagcaac agtaaaagct ggagaaatag cagcagtgcc agtaacatta   1320
acaagtgttc catcaactgg aatagcaact gctgaagcac aagtaagttt tgatgcaaca   1380
ttattagaag tagcatcagt aactgctgga gatatcgtat taaatccaac agtaaacttc   1440
tcttatacag taacggaaa tgtaataaaa ttattattcc tagatgatac attaggaagc    1500
caattaatta gtaaagatgg agttttgta acaataaact tcaaagcaaa agctgtaaca    1560
agcacagtaa caacaccagt tacagtatca ggaacacctg tatttgcaga tggtacatta   1620
gcagaagtac aatctaaaac agcagcaggt agcgttacaa taaatattgg agatcctata   1680
gcggccgcac tcgagcacca ccaccaccac cac                                1713

SEQ ID NO: 7            moltype = AA    length = 91
FEATURE                 Location/Qualifiers
REGION                  1..91
                        note = polypeptide sequence of CBM3
source                  1..91
                        mol_type = protein
                        organism = synthetic construct
SEQUENCE: 7
VEFYNSNKSA QTNSITPIIK ITNTSDSDLN LNDVKVRYYY TSDGTQGQTF WCDHAGALLG     60
NSYVDNTSKV TANFVKETAS PTSTYDTYVE F                                   91

SEQ ID NO: 8            moltype = AA    length = 273
FEATURE                 Location/Qualifiers
REGION                  1..273
                        note = polypeptide sequence of PETase
source                  1..273
                        mol_type = protein
                        organism = synthetic construct
SEQUENCE: 8
MELGTXXXXQ TNPYARGPNP TAASLEASAG PFTVRSFTVS RPSGYGAGTV YYPTNAGGTV     60
GAIAIVPGYT ARQSSIKWWG PRLASHGFVV ITIDTNSTLD QPSSRSSQQM AALRQVASLN    120
GTSSSPIYGK VDTARMGVMG HSMGGGGSLI SAANNPSLKA AAPQAPWDSS TNFSSVTVPT    180
LIFACENDSI APVNSSALPI YDSMSRNAKQ FLEINGGSHF CANSGNSNQA LIGKKGAAWM    240
KRFMDNDTRY STFACENPNS TRVSDFRTAN CSL                                 273

SEQ ID NO: 9            moltype = DNA   length = 819
FEATURE                 Location/Qualifiers
misc_feature            1..819
                        note = polynucleotide sequence of PETase
source                  1..819
                        mol_type = other DNA
                        organism = synthetic construct
SEQUENCE: 9
atggagctcg gtaccathga rggncgncag accaatccgt atgcgcgcgg ccccaaccct     60
accgccgcct cgttggaagc cagcgcggga cccttttacc ttcgtagctt taccgttagc    120
```

```
cgtccgtccg gatatggtgc agggaccgtc tattacccaa ccaatgcagg cggcaccgtt   180
ggcgcgattg caatcgtccc cgggtacacc gcgcgtcaaa gcagcattaa gtggtggggt   240
ccgcgcttag ctagccatgg cttttgtggt attaccatcg atacgaacag cactctagac   300
cagcccagca gccgtagctc gcaacagatg ccgcgcttc gtcaagttgc gagcttgaac    360
gggaccagca gtagcccgat ttacggaaag gtcgatactg cccgcatggt tgtgatgggc   420
cactcaatgg ggggcggcgg ttcacttatt agccgccgcga acaacccgag tttaaaagca   480
gcggcaccgc aggcgccatg ggactcttca accaacttca gcagtgttac cgtgccgacg   540
ctgattttcg cgtgcgagaa tgatagcatt gcaccggtga acagcagcgc gctgccgatt   600
tatgatagca tgtcccgcaa cgcaaaaacag ttctggaaa ttaacggcgg tagccactc    660
tgtgccaact ctgggaacag caaccaggca ctgatcggaa aaaaggggc tgcatggatg   720
aaacgattca tggataatga caccgttac tcaaccttcg cctgtgagaa tcccaacagc    780
acacgcgtgt cggattttcg caccgcgaac tgttccctc                          819

SEQ ID NO: 10           moltype = AA   length = 329
FEATURE                 Location/Qualifiers
REGION                  1..329
                        note = polypeptide sequence of CALB
source                  1..329
                        mol_type = protein
                        organism = synthetic construct
SEQUENCE: 10
MELGTXXXXA LPSGSDPAFS QPKSVLDAGL TCQGASPSSV SKPILLVPGT GTTGPQSFDS    60
NWIPLSTQLG YTPCWISPPP FMLNDTQVNT EYMVNAITAL YAGSGNNKLP VLTWSQGGLV   120
AQWGLTFFPS IRSKVDRLMA FAPDYKGTVL AGPLDALAVS APSVWQQTTG SALTTALRNA   180
GGLTQIVPTT NLYSATDEIV QPQVSNSPLD SSYLFNGKNV QAQAVCGPLF VIDHAGSLTS   240
QFSYVVGRSA LRSTTGQARS ADYGITDCNP LPANDLTPEQ KVAAAALLAP AAAIVAGPK   300
QNCEPDLMPY ARPFAVGKRT CSGIVTPSL                                    329

SEQ ID NO: 11           moltype = DNA   length = 987
FEATURE                 Location/Qualifiers
misc_feature            1..987
                        note = polynucleotide sequence of CALB
source                  1..987
                        mol_type = other DNA
                        organism = synthetic construct
SEQUENCE: 11
atggagctcg gtaccathga rggncgngca ttgccgtcag gttctgaccc ggcctttagc    60
cagccgaagt ctgttctgga tgctggcctg acatgtcagg gtgcaagccc gtcgtccgta   120
agcaaaccaa ttctgcttgt accaggcacg ggcactacgg gcccgcagag ctttgattct   180
aattggattc ccctgtctac ccagcttggg tacacccctt gttggattag cccgcctccc   240
ttcatgctga cgatacaca agtgaatact gagtacatgg tcaacgcaat taccgccctt   300
tatgcgggaa gtggtaacaa taaacttccc gtgctgacat ggagtcaggg gggcctggtg   360
gcacagtggg gattgacgtt tttcccatcg atccgctcga agttgatcg tctgatgcaa   420
tttgcgcctg attataaagg cacagtgctc gcggggccat tagatgccct ggctgtgtca   480
gcacctagtg tctggcaaca gacgaccggt tccgcgctga cgaccgccct ccggaacgca   540
ggtggactga cccaaattgt gccgacaacc aacttgtata cgccaccgaa cgaaattgtt   600
cagccgcagg tctccaattc gcctctcgat tcaagctctc tgttaacggc aaaaaatgta   660
caggcacagg ctgtttgcgg gccattattc gtcatcgacc atgccggtag cttaacctcc   720
cagttcagtt acgtggttgg tcgctctgcc ctgcgtagta ccacgggcca agcgcgctca   780
gcggactacg gtatcactga ttgcaatccg ttaccggcga atgacctgac tccggaacaa   840
aaggtagcgg ctgcggcttt gttagcgccg gccgctgccg cgattgtggc aggtcctaaa   900
caaaactgtg aaccggatct gatgccctat gcccgtccgt ttgcggtcgg caaacgtact   960
tgctcaggta tcgttacgcc aagctta                                     987

SEQ ID NO: 12           moltype = AA   length = 77
FEATURE                 Location/Qualifiers
REGION                  1..77
                        note = polypeptide sequence of dockerin module
source                  1..77
                        mol_type = protein
                        organism = synthetic construct
SEQUENCE: 12
GSAGSAAGSG EFDVNKDGKV NAIDYAVLKS ILLGTNTNVD LSVSDMNKDG KVNALDLAVL    60
KKMLLDYKDD DDKLQSR                                                  77

SEQ ID NO: 13           moltype = DNA   length = 1323
FEATURE                 Location/Qualifiers
misc_feature            1..1323
                        note = polynucleotide sequence of Endo-beta-1,4-Glucanase-B
source                  1..1323
                        mol_type = other DNA
                        organism = synthetic construct
SEQUENCE: 13
atgaataaaa gattatcacg gggaaagata tctcttttag catcagtttt cgttaccaca    60
acttttatgg ggggagtaaa tgttctcgca tctacagcta agacaggtat tcgtgacata   120
acttctcaac aagttgttaa ggaaatgaag gttggttgga ctttaggaaa tacaatggat   180
gctacaggag gagaaacaaa ttgggggaat ccattaacaa cacatgccat gattgacaaa   240
gtaaaagcag caggctttaa tacttttaag cttccaataa cttgggatgg tcatattgga   300
gcagcaccag attatgctat tgatgcaaca tggatgaata gagtcgaaga aatagcaaat   360
```

```
tatgcttttg ataataatat gtatgttata ataaatcttc atcacgaaga tggatggctt   420
aagccttatt atgccaatga ggctgaagta aaagctaaaa tcacaaaagt atggacacaa   480
attgcaaatc gctttaaaga ttatggggat tatctaattt ttgaaacaat gaatgaacct   540
cgtccagtag gcgcagctga tgaatggtct ggtggctcct atgaaaatcg agatatggtt   600
aatagatata atttaacagc ggtaaacact attagagcta ctggtggaaa taatgcatta   660
aggcacatta tggttccaac tcttgcagca gcagcactta gcacaacaat gaatgattac   720
atagtaccaa ataatgatag cagagttata gtatccttac atatgtattc accatatttc   780
ttctctgcag atcttactag tcaatggact acagcaactt ggggaagtga tgctgataag   840
gctgcactaa gtgctgactt tgatgcagtt tataataagt ttgttaagaa tggaagagct   900
gtagttattg gcgaaatggg aacaatcaat aagaataatt tagattctag agtgaaacat   960
gcagaatatt atgctaaaga agcaacagtt agagggataa ctcctatatg gtgggataat  1020
ggatattgtg ttgctggaaa agagcaaacc ttcggaatat taatagaaa  gaatcttact  1080
tggtgttgtc cagaagttat gcaagctttc ataagaggag caggtgccac acaaaactca  1140
acttctattt cactaggtta tgttaacaaa gatggaaagg taaatgctat cgattatgca  1200
gtgcttaaat caattctttt aggtacaaat actaacgttg atttatcagt atcagacatg  1260
aataaggatg gtaaagtaaa tgctttggat ttagctgttc ttaaaaaaat gcttttaagc  1320
taa                                                                1323

SEQ ID NO: 14            moltype = DNA   length = 28
FEATURE                  Location/Qualifiers
misc_feature             1..28
                         note = forward primer for PETase gene amplification
source                   1..28
                         mol_type = other DNA
                         organism = synthetic construct
SEQUENCE: 14
tataggtacc aacttccccc gtgcctcg                                      28

SEQ ID NO: 15            moltype = DNA   length = 34
FEATURE                  Location/Qualifiers
misc_feature             1..34
                         note = reverse primer for PETase gene amplification
source                   1..34
                         mol_type = other DNA
                         organism = synthetic construct
SEQUENCE: 15
ggagccagcg gatccgaggg aacagttcgc ggtg                               34

SEQ ID NO: 16            moltype = DNA   length = 30
FEATURE                  Location/Qualifiers
misc_feature             1..30
                         note = forward primer for CALB gene amplification
source                   1..30
                         mol_type = other DNA
                         organism = synthetic construct
SEQUENCE: 16
attaggtacc atggcattgc cgtcaggttc                                    30

SEQ ID NO: 17            moltype = DNA   length = 40
FEATURE                  Location/Qualifiers
misc_feature             1..40
                         note = reverse primer for CALB gene amplification
source                   1..40
                         mol_type = other DNA
                         organism = synthetic construct
SEQUENCE: 17
ggagccagcg gatcctaagc ttggcgtaac gatacctgag                         40

SEQ ID NO: 18            moltype = DNA   length = 31
FEATURE                  Location/Qualifiers
misc_feature             1..31
                         note = forward primer for dockerin gene amplification_1
source                   1..31
                         mol_type = other DNA
                         organism = synthetic construct
SEQUENCE: 18
gcgaactgtt ccctcggatc cgctggctcc g                                  31

SEQ ID NO: 19            moltype = DNA   length = 30
FEATURE                  Location/Qualifiers
misc_feature             1..30
                         note = forward primer for dockerin gene amplification_2
source                   1..30
                         mol_type = other DNA
                         organism = synthetic construct
SEQUENCE: 19
gttacgccaa gcttaggatc cgctggctcc                                    30

SEQ ID NO: 20            moltype = DNA   length = 48
```

```
FEATURE                 Location/Qualifiers
misc_feature            1..48
                        note = reverse primer for dockerin gene amplification
source                  1..48
                        mol_type = other DNA
                        organism = synthetic construct
SEQUENCE: 20
gcgcctgcag taaaagcatt ttttaagaa cagctaaatc caaagcat              48

SEQ ID NO: 21           moltype = DNA   length = 28
FEATURE                 Location/Qualifiers
misc_feature            1..28
                        note = recombinant PETase_Primer_Forward F
source                  1..28
                        mol_type = other DNA
                        organism = synthetic construct
SEQUENCE: 21
tataggtacc aacttccccc gtgcctcg                                   28

SEQ ID NO: 22           moltype = DNA   length = 34
FEATURE                 Location/Qualifiers
misc_feature            1..34
                        note = recombinant PETase_Primer_Forward R
source                  1..34
                        mol_type = other DNA
                        organism = synthetic construct
SEQUENCE: 22
ggagccagcg gatccgaggg aacagttcgc ggtg                            34

SEQ ID NO: 23           moltype = DNA   length = 31
FEATURE                 Location/Qualifiers
misc_feature            1..31
                        note = recombinant PETase_Primer_Reverse F
source                  1..31
                        mol_type = other DNA
                        organism = synthetic construct
SEQUENCE: 23
gcgaactgtt ccctcggatc cgctggctcc g                               31

SEQ ID NO: 24           moltype = DNA   length = 48
FEATURE                 Location/Qualifiers
misc_feature            1..48
                        note = recombinant PETase_Primer_Reverse R
source                  1..48
                        mol_type = other DNA
                        organism = synthetic construct
SEQUENCE: 24
gcgcctgcag taaaagcatt ttttaagaa cagctaaatc caaagcat              48

SEQ ID NO: 25           moltype = DNA   length = 30
FEATURE                 Location/Qualifiers
misc_feature            1..30
                        note = recombinant CALB_Primer_Forward F
source                  1..30
                        mol_type = other DNA
                        organism = synthetic construct
SEQUENCE: 25
attaggtacc atggcattgc cgtcaggttc                                 30

SEQ ID NO: 26           moltype = DNA   length = 40
FEATURE                 Location/Qualifiers
misc_feature            1..40
                        note = recombinant CALB_Primer_Forward R
source                  1..40
                        mol_type = other DNA
                        organism = synthetic construct
SEQUENCE: 26
ggagccagcg gatcctaagc ttggcgtaac gatacctgag                      40

SEQ ID NO: 27           moltype = DNA   length = 30
FEATURE                 Location/Qualifiers
misc_feature            1..30
                        note = recombinant CALB_Primer_Reverse F
source                  1..30
                        mol_type = other DNA
                        organism = synthetic construct
SEQUENCE: 27
gttacgccaa gcttaggatc cgctggctcc                                 30
```

```
SEQ ID NO: 28          moltype = DNA  length = 48
FEATURE                Location/Qualifiers
misc_feature           1..48
                       note = recombinant CALB_Primer_Reverse R
source                 1..48
                       mol_type = other DNA
                       organism = synthetic construct
SEQUENCE: 28
gcgcctgcag taaaagcatt tttttaagaa cagctaaatc caaagcat              48

SEQ ID NO: 29          moltype = DNA  length = 30
FEATURE                Location/Qualifiers
misc_feature           1..30
                       note = forward primer for mCbpA gene amplification
source                 1..30
                       mol_type = other DNA
                       organism = synthetic construct
SEQUENCE: 29
ccatggcagc gacatcatca atgtcagttg                                  30

SEQ ID NO: 30          moltype = DNA  length = 43
FEATURE                Location/Qualifiers
misc_feature           1..43
                       note = reverse primer for mCbpA gene amplification
source                 1..43
                       mol_type = other DNA
                       organism = synthetic construct
SEQUENCE: 30
caggtagcgt tacaataaat attggagatc ctatagactc gag                   43
```